United States Patent [19]

Kobayashi et al.

[11] 4,011,254

[45] Mar. 8, 1977

[54] PROCESS FOR THE PURIFICATION OF DIAMINOMALEONITRILE

[75] Inventors: Tatsumi Kobayashi; Yutaka Takakura; Sadafumi Yoshino; Yoshiaki Fukuda, all of Kurashiki, Japan

[73] Assignee: Nippon Soda Company Limited, Tokyo, Japan

[22] Filed: Aug. 19, 1975

[21] Appl. No.: 605,865

[30] Foreign Application Priority Data

Sept. 3, 1974 Japan ............................ 49-101228

[52] U.S. Cl. .......................................... 260/465.5 R
[51] Int. Cl.$^2$ .............. C07C 120/00; C07C 121/45
[58] Field of Search .............................. 260/465.5 R

[56] References Cited

UNITED STATES PATENTS

| | | | |
|---|---|---|---|
| 2,818,423 | 12/1957 | Carter | 260/465.5 R |
| 3,564,039 | 2/1971 | Webster | 260/465.5 R |
| 3,629,318 | 12/1971 | Webster | 260/465.5 R |
| 3,701,797 | 10/1972 | Okada et al. | 260/465.5 R |
| 3,842,115 | 10/1974 | Hamamoto et al. | 260/465.5 R |

*Primary Examiner*—Joseph P. Brust
*Attorney, Agent, or Firm*—George B. Oujevolk

[57] ABSTRACT

Diaminomaleonitrile which is produced by the tetramerization of hydrogen cyanide is purified by heating a crude diaminomaleonitrile in an inert liquid or in an inert atmosphere at a temperature of 90° to 140° C, preferably 100° to 120° C, and then extracting pure diaminomaleonitrile having a purity of about 99% from said heated crude diaminomaleonitrile with a solvent.

7 Claims, No Drawings

PROCESS FOR THE PURIFICATION OF DIAMINOMALEONITRILE

BACKGROUND OF THE INVENTION

The invention relates to a process for the purification of crude diaminomaleonitrile which is produced by using hydrogen cyanide as a raw material.

Diaminomaleonitrile is a useful compound as an intermediate for glycine, 2-amino-4,5-dicyanoimidazole, 4-aminoimidazole-5-carboxamide, xanthine, hypoxanthine, cafeine, theophilline, adenine, guanine and the like.

The development in the method for the purification of diaminomaleonitrile is very important because a highly pure diaminomaleonitrile is required when it is used as a intermediate for food additives or medicines.

Methods by means of sublimation, formation of complex, and extraction are well-known for the purification of diaminomaleonitrile. The sublimation method is disadvantageous due to a low yield. Also, the method by formation of complex is disadvantageous due to the complicated operation and is difficult to be employed for an industrial process. The extraction method is usually employed for the purification of diaminomaleonitrile.

Japanese Patent Publication (before examination) No. 30319/1974 discloses a process for the purification of diaminomaleonitrile by extraction, wherein diaminomaleonitrile is extracted with an ester of acetic acid the amount of which is 16 to 20 times the weight of a crude diaminomaleonitrile, and after adding the same amount of hydrocarbon as the ester of acetic acid to the extract, the ester is removed by distillation to precipitate and separate diaminomaleonitrile having a purity of 95 to 98%.

According to Japanese Patent Publication (before examination) No. 30321/1974, a mixed solvent consisting of a group of ketones, alcohols, nitriles and ethers, and a group of hydrocarbons and halogenated hydrocarbons is used as an extraction solvent. The amount of the solvent is 33 to 40 times the weight of a crude diaminomaleonitrile and diaminomaleonitrile having a purity of 93 to 95% is obtained.

Japanese Patent Publication (before examination) No. 81818/1973 also discloses an extraction method. In the method, a crude diaminomaleonitrile having a purity of about 90% is washed with a hydrocarbon or a halogenated aliphatic hydrocarbon by an amount of 15 times the weight of the crude diaminomaleonitrile and then, a purified diaminomaleonitrile having a purity of 99 to 99.5% is obtained by extraction with methyl acetate, ethyl acetate, isopropyl alcohol or the like the amount of which is 15 to 25 times the weight of the crude diaminomaleonitrile.

When diaminomaleonitrile is produced by the tetramerization of hydrogen cyanide, it is unavoidable that a higher polymer than tetramer is formed simultaneously with the production of diaminomaleonitrile. In addition, said higher polymer is liable to be contained in a purified product by extraction due to its solubility property which is similar to that of diaminomaleonitrile.

Consequently, the selectivity to diaminomaleonitrile must be given greater consideration than the solubility of diaminomaleonitrile when selecting an extraction solvent for the purification of diaminomaleonitrile, and the amount used of the extraction solvent is very large in the conventional extraction method through the purified product has a considerbly high purity.

SUMMARY OF THE INVENTION

The inventors have found that the heating of a crude diaminomaleonitrile including a higher polymer makes the purification by extraction easy.

The higher polymer consists of a component which is insoluble in a solvent for the extraction of diaminomaleonitrile (this component being hereinafter referred to as "insoluble higher polymer"), and another component which is soluble in a solvent for the extraction and is the obstacle to the purification by extraction (this component being hereinafter referred to as "soluble higher polymer").

The soluble higher polymer converts to the insoluble higher polymer by heating it at a temperature of about 100° C, so that, consequently, the purification by extraction becomes easy. In other words, it is not necessary to take into account the selectivity of the extraction solvent to diaminomaleonitrile, and a solvent having a high solubility of diaminomaleonitrile can be employed.

It is an object of the invention to provide an improved process for the purification of diaminomaleonitrile.

It is still more specific object of the invention to improve the extraction method for the purification of diaminomaleonitrile.

Other and further objects, features and advantages of the invention will appear more fully from the following description.

DETAILED DESCRIPTION

The invention is a process for the purification of diaminomaleonitrile which comprises heating a crude diaminomaleonitrile produced from hydrogen cyanide, and then extracting a pure diaminomaleonitrile with a solvent from said heated crude diaminomaleonitrile.

The heating of crude diaminomaleonitrile may be carried out in an inert organic liquid or in an inert atmosphere of air or nitrogen.

Where the thermal treatment is carried out in an inert organic liquid, the kind of the liquid used is not critical so long as it is inert to diaminomaleonitrile under the reaction conditions of the thermal treatment. However, a liquid which has a boiling point of 90° C or above and does not dissolve diaminomaleonitrile is preferable. If the boiling point of the inert organic liquid is below 90° C, the temperature of the thermal treatment is not enough high to complete the treatment unless a higher pressure than atmosphere is employed. If a liquid which dissolves diaminomaleonitrile is used, the post-treatment is complicated. In other words, evaporation of the liquid becomes necessary before the extraction, and, in addition, the decomposition of diaminomaleonitrile increases as the solubility increases.

Consequently, an inert organic liquid in which diaminomaleonitrile is least soluble is preferable for the thermal treatment.

In other words, where a liquid is used, it is preferable to heat a suspension of diaminomaleonitrile therein.

In the invention, the liquid in which diaminomaleonitrile is soluble includes liquids having a solubility of 0.1% or less, preferably 0.01% or less, by weight.

The preferable liquids for the thermal treatment are, for example, alkyl-benzenes such as toluene, xylene and ethylbenzene, halogenated aromatic hydrocarbons such as monochlorobenzene and dichlorobenzene (o-, m-, p-,), and halogenated aliphatic hydrocarbons such as 1,2-dichloropropane and perchloroethylene. These organic liquids do not dissolve diaminomaleonitrile and have a boiling point of 90° C or above.

The amount of the liquid selected is such that a slurry of a crude diaminomaleonitrile therein can be stirred. The amount is at least 1.5 times the weight of crude diaminomaleonitrile, preferably 2 to 10 times.

The thermal treatment is generally carried out at a temperature of 90° to 140° C, preferably from 100° to 120° C. In case the temperature is below 90° C, the conversion of the soluble higher polymer to the insoluble higher polymer is not sufficient. In case the temperature is above 140° C, the decomposition of diaminomaleonitrile increases.

The time necessary for the thermal treatment depends on the temperature, being generally from 0.5 to 5 hours. For example, where the temperature is 100° to 120° C, the thermal treatment is usually carried out for 1 to 3 hours.

The extraction of diaminomaleonitrile from the crude product resulting from the above-mentioned thermal treatment is very easy, because all of the impurity included in the original crude product has been changed into the insoluble higher polymer which is insoluble in the extraction solvents used for the extraction of diaminomaleonitrile. In other words, the extraction solvent may be selected without considering the selectivity thereof to diaminomaleonitrile and to the impurity with which it is associated.

Consequently, the thermal treatment provides the advantage that a solvent having a relatively higher solubility for diaminomaleonitrile can be used for the extraction.

Also, while diaminomaleonitrile decomposes by the thermal treatment, the decomposition, however, can be suppressed within several percents by maintaining the temperature and the heating time in the optimum range.

After the thermal treatment, the crude diaminomaleonitrile is separated by filtration and highly pure diaminomaleonitrile is obtained by extraction therefrom. In case that the thermal treatment is carried out in an inert atmosphere of air or nitrogen, the extraction is directly carried out after the thermal treatment.

Solvents which are inert to diaminomaleonitrile and dissolve it are all employable as extraction solvents. Useful extraction solvents include alcohols such as methyl alcohol, ethyl alcohol, isopropyl alcohol and butyl alcohol, ethers such as diethyl ether, dioxane and tetrahydrofuran, esters of lower fatty acids such as methyl acetate and ethyl acetate, nitriles such as acetonitrile, propionitrile and butyronitrile, ketones such as acetone, methylethylketone and methylisobutylketone, and water. From the industrial viewpoint, it is preferable to use an extraction solvent which dissolves diaminomaleonitrile well. Such solvents are, for example, methyl alcohol, tetrahydrofuran, dioxane, acetonitrile, and methyl ethyl ketone.

Ordinary extraction methods are employable in the invention. For example, the heated, crude diaminomaleonitrile may be added to a solvent and the mixture is filtered to remove the insoluble higher polymer.

The conditions for extraction vary with the solvent. For example, in the case of using the above-mentioned extraction solvents which dissolve diaminomaleonitrile well, a useful amount of a solvent is 4 to 8 times the weight of crude diaminomaleonitrile. As a matter of course, a solvent of more than 8 times may be used, but it is, however, disadvantageous from an industrial viewpoint. The temperature for the extraction also varies with the solvent; however, a range of room temperature to 70° C is preferable. The time for the extraction depends on the method of extraction and the solvent, and the range of 15 to 30 minutes is generally sufficient. Diaminomaleonitrile becomes free from the insoluble higher polymer of hydrogen cyanide by the extraction process. After the extraction, distillation of the solvent gives purified diaminomaleonitrile having a purity of 97 to 99.5%.

The above-described process for the purification of diaminomaleonitrile can be applied to the purification of all the crude diaminomaleonitrile which is produced by using hydrogen cyanide as a raw material. The said crude diaminomaleonitrile includes the diaminomaleonitrile which is produced by tetramerization of hydrogen cyanide and produced from an intermediate which is prepared from hydrogen cyanide.

According to the invention, therefore, highly pure diaminomaleonitrile is easily obtained by an industrially advantageous process. In addition, the pure diaminomaleonitrile obtained by the purification of the invention is extremely stable; that is, during storage or transportation the purity and the appearance do not change and the pure diaminomaleonitrile also has a property of thermostability, though the pure product having a purity of about 99% which is obtained by repeating the ordinal purification, i.e., recrystallization, extraction, gradually changes in purity and appearance, and gradually evolves hydrogen cyanide, which is very dangerous.

The following examples are intended to aid in the understanding of the invention, and variations may be made by one skilled in the art without departing from the spirit and scope of the invention.

EXAMPLE 1.

The composition of the crude diaminomaleonitrile which was obtained by tetramerizing hydrogen cyanide in toluene as a solvent in the presence of triethylamine and diphenyldisulfide as catalysts was as follows.
Diaminomaleonitrile 80.2 wt%
Soluble higher polymer in acetonitrile 6.5 wt%
Insoluble higher polymer in acetonitrile 13.3 wt%

In 40g of toluene was suspended 10 g of the above-mentioned crude diaminomaleonitrile. The suspension was refluxed at 110° C for 3 hours. After cooling, the crude diaminomaleonitrile was separated by filtration and dried. The residue was added to 50g of acetonitrile and stirred at 55° to 60° C for 30 minutes and then, the mixture was filtered to remove the higher polymer which is insoluble in acetonitrile.

The removal of acetonitrile from the filtrate by a film-evaporator gave 7.8 g of pale brown purified diaminomaleonitrile.

The product was analyzed by ultraviolet spectrum ($\lambda$ max 296 m$\mu$). As the result, the purity was 98.4%.

Comparative Example 1

To 50 g of acetonitrile was added 10 g of the crude diaminomaleonitrile having the same composition as in Example 1. The mixture was stirred at 55° to 60° C for 30 minutes, and filtered. Acetonitrile was distilled away from the filtrate by a film-evaporator to yield 8.6 g of brown purified diaminomaleonitrile.

The product was analyzed as in Example 1, and the purity was 92.5%.

EXAMPLE 2

In 80 g of xylene was suspended 20 g of the same crude diaminomaleonitrile as in Example 1. The mixture was refluxed at 140° C for 1 hour. After cooling, the crude diaminomaleonitrile was separated by filtration and dried. The residue was added to 100 g of acetonitrile and stirred at 70° C for 20 minutes, and then, the mixture was filtered. The removal of acetonitrile from the filtrate by a film-evaporator gave 14.1 g of pale brown purified product. The purity of the product was 98.8%.

EXAMPLE 3

In 80 g of xylene was suspended 20 g of crude diaminomaleonitrile which was obtained by tetramerization of hydrogen cyanide in xylene as a solvent in the presence of triethylamine and diphenyldisulfide and had a purity of 73.7%, and was stirred at 120° C for 1 hour. After cooling, the crude diaminomaleonitrile was separated by filtration and dried. The residue was added to 90 g of methyl alcohol and was stirred at 40° C for 30 minutes and then, the mixture was filtered. The removal of methyl alcohol from the filtrate by a film-evaporator gave 13.6 g of pale brown purified product. The purity of the product was 97.7%.

EXAMPLE 4

In an atmosphere of heated air at 120° C was placed 20 g of the same crude diaminomaleonitrile as in Example 3 for 3 hours. The crude diaminomaleonitrile was then added to 140 g of ethyl alcohol and the mixture was stirred for 15 minutes at 60° C, and was filtered. Ethyl alcohol in the filtrate was distilled away by a film-evaporator. There remained 13.5 g of pale brown purified product which had a purity of 99.0%.

EXAMPLE 5

In an atmosphere of heated air at 120° C was placed 20 g of the same crude diaminomaleonitrile as in Example 1 for 1 hour. The crude diaminomaleonitrile was then added to 100 g of acetonitrile and the mixture was stirred for 15 minutes at 70° C, and was filtered. Acetonitrile in the filtrate was distilled away by a film-evaporator. There remained 14.9 g of pale brown purified product which had a purity of 99.3%.

EXAMPLE 6

In an atmosphere of heated nitrogen gas at 120° C was placed 20 g of the same crude diaminomaleonitrile as in Example 1 for 1 hour. The crude diaminomaleonitrile was then added to 100 g of acetonitrile and the mixture was stirred for 15 minutes at 70° C, and was filtered. Acetonitrile in the filtrate was distilled away by a film-evaporator. There remained 15.0 g of pale brown purified product which had a purity of 98.8%.

EXAMPLE 7

Crude diaminomaleonitrile (20 g) having a purity of 62% which was produced by tetramerization of hydrogen cyanide in acetonitrile in the presence of triethylamine, was suspended in 80 g of toluene and was stirred at 110° C for 3 hours. After cooling, the crude diaminomaleonitrile was separated by filtration, dried and added to 100 g of acetonitrile. The mixture was stirred at 55° to 60° C for 30 minutes and then, the mixture was filtered. Acetonitrile in the filtrate was distilled away by a film-evaporator. There remained 11.8 g of diaminomaleonitrile which had a purity of 99.1%.

EXAMPLE 8

Crude diaminomaleonitrile (20 g) having a purity of 65% which was produced by tetramerization of hydrogen cyanide in toluene in the presence of dicyan, was treated as in Example 3. As the result, 11.9 g of diaminomaleonitrile which had a purity of 98.5% was obtained.

EXAMPLE 9

Crude diaminomaleonitrile (20 g) having a purity of 63% which was produced by reduction of diiminosuccinonitrile with hydrogen sulfide in methylene chloride, was treated as in Example 5. As the result, 11.8 g of diaminomaleonitrile which had a purity of 99.2% was obtained.

EXAMPLE 10

Pure diaminomaleonitrile obtained as in Example 1 was allowed to stand for one month at 50° C but the purity and the appearance did not change. When allowed to stand for one week at 70° C the purity and the appearance also did not change. In both cases, the evolution of hydrogen cyanide was not detected.

Comparative Example 2

The same crude diaminomaleonitrile obtained as in Example 1 was purified by repeating the recrystallization with water using active carbon until the purity became 98.6%. The pure diaminomaleonitrile thus obtained, which had a color of pale brown, was allowed to stand as in Example 10. The diaminomaleonitrile turned grayish brown and the evolution of hydrogen cyanide was detected.

What we claim is:

1. A process for the recovery of diaminomaleonitrile, in essentially pure form, from a crude mixture produced by the tetramerization of hydrogen cyanide and containing (a) diaminomaleonitrile, (b) a higher hydrogen cyanide polymer than the tetrameric diaminomaleonitrile which is soluble in a solvent for diaminomaleonitrile, and (c) a higher hydrogen cyanide polymer than tetrameric diaminomaleonitrile which is insoluble in a solvent for diaminomaleonitrile, comprising heating said crude mixture in a gaseous medium which is inert towards diaminomaleonitrile and is selected from the group consisting of air and nitrogen, at a temperature of about from 90° C to 140° C for about from 0.5 to 5 hours whereby said higher hydrogen cyanide polymer which is soluble in a diaminomaleonitrile solvent is converted to additional higher hydrogen cyanide polymer which is insoluble in a diaminomaleonitrile solvent, separating the diaminomaleonitrile from the insoluble higher polymer by extraction with a diaminomaleonitrile solvent, and removing the solvent from the resulting diaminomaleonitrile solution to obtain diaminomaleonitrile in a purity of about 99%.

2. The process of claim 1 wherein the diaminomaleonitrile solvent is a member selected from the group consisting of a lower alkanol, an ether, an ester of a lower fatty acid, a nitrile, a ketone, and water.

3. The process of claim 2 wherein the lower alkanol is a member selected from the group consisting of methanol, ethanol, isopropanol, and butanol.

4. The process of claim 2 wherein the ether is a member selected from the group consisting of diethyl ether, dioxane, and tetrahydrofuran.

5. The process of claim 2 wherein the ester of a lower fatty acid is a member selected from the group consisting of methyl acetate and ethyl acetate.

6. The process of claim 2 where the nitrile is acetonitrile.

7. The process of claim 2 wherein the ketone is a member selected from the group consisting of acetone, methyl ethyl ketone, and methyl isobutyl ketone.

* * * * *